United States Patent
Palmer

(10) Patent No.: US 10,589,061 B2
(45) Date of Patent: Mar. 17, 2020

(54) PACKAGED PRECISION-LUBRICATED READY-TO-USE INTERMITTENT URINARY CATHETER

(71) Applicant: CURE MEDICAL, LLC, Newport Beach, CA (US)

(72) Inventor: Timothy Palmer, Stillwater, MN (US)

(73) Assignee: CURE MEDICAL, LLC, New Port Beach, CA (US)

( * ) Notice: Subject to any disclaimer, the term of this patent is extended or adjusted under 35 U.S.C. 154(b) by 0 days.

(21) Appl. No.: 16/385,440

(22) Filed: Apr. 16, 2019

(65) Prior Publication Data

US 2019/0240445 A1     Aug. 8, 2019

Related U.S. Application Data

(63) Continuation-in-part of application No. 15/130,337, filed on Apr. 15, 2016, now Pat. No. 10,293,136.

(51) Int. Cl.
| | |
|---|---|
| *A61M 25/00* | (2006.01) |
| *B65B 5/04* | (2006.01) |
| *B65B 31/02* | (2006.01) |
| *B65B 51/10* | (2006.01) |

(52) U.S. Cl.
CPC ......... *A61M 25/002* (2013.01); *B65B 5/045* (2013.01); *B65B 31/02* (2013.01); *B65B 51/10* (2013.01); *A61M 2025/0046* (2013.01); *A61M 2205/0222* (2013.01); *A61M 2207/00* (2013.01)

(58) Field of Classification Search
CPC ............ A61M 25/0017; A61M 25/002; A61M 25/0111; A61M 25/0113; B65D 75/30; B65D 81/22; B65B 11/50; B65B 11/52; B65B 5/028; B65B 5/04; B65B 5/045; B65B 51/02; B65B 31/02; B65B 31/00; B65B 55/22; A61B 50/30; A61B 50/20
USPC ........... 53/431, 433, 471; 206/364, 571, 363
See application file for complete search history.

(56) References Cited

U.S. PATENT DOCUMENTS

| | | | |
|---|---|---|---|
| 3,345,988 A | | 10/1967 | Vitello |
| 3,353,325 A | * | 11/1967 | Jensen ..................... B65B 11/52 |
| | | | 206/484 |
| 3,648,428 A | * | 3/1972 | Colburn ................... B65B 11/52 |
| | | | 206/205 |
| 3,726,057 A | * | 4/1973 | Kemble ........... A61B 17/06133 |
| | | | 422/40 |

(Continued)

FOREIGN PATENT DOCUMENTS

| | | |
|---|---|---|
| CN | 204840604 U | 12/2015 |
| EP | 0677299 A1 | 10/1995 |

(Continued)

*Primary Examiner* — Chelsea E Stinson
*Assistant Examiner* — Thomas M Wittenschlaeger
(74) *Attorney, Agent, or Firm* — Sherrill Law Offices, PLLC

(57) ABSTRACT

A method of packaging a ready to use intermittent urinary catheter by (i) placing lubricant within a pocket formed in a base film proximate a first end of the pocket, (ii) placing a catheter within the pocket with the insertion end of the catheter proximate the first end of the pocket, (iii) partially sealing the catheter within the pocket between the base film and a cover film, (iv) pulling a vacuum within the pocket to effect controlled circumferential flow of lubricant around the insertion end portion of the catheter, and then (v) fully sealing the pocket.

13 Claims, 6 Drawing Sheets

(56) References Cited

U.S. PATENT DOCUMENTS

| | | |
|---|---|---|
| 3,750,875 A | 8/1973 | Juster |
| 3,754,372 A * | 8/1973 | Perdue .................. B65B 11/52 53/511 |
| 3,934,721 A | 1/1976 | Juster et al. |
| 3,967,728 A | 7/1976 | Gordon et al. |
| 4,230,115 A | 10/1980 | Walz, Jr. et al. |
| 4,611,456 A * | 9/1986 | Gillio-tos ............ B65D 75/305 156/287 |
| 4,833,862 A * | 5/1989 | Bortolani ............ B65D 75/305 426/396 |
| 5,147,341 A | 9/1992 | Starke et al. |
| 5,226,530 A | 7/1993 | Golden |
| 5,607,055 A | 3/1997 | Bettinger |
| 5,782,344 A * | 7/1998 | Edwards ............... B65B 9/2028 206/217 |
| 5,895,374 A | 4/1999 | RØdsten |
| 6,004,305 A | 12/1999 | Hursman et al. |
| 6,053,905 A | 4/2000 | Daignault, Jr. et al. |
| 6,059,107 A * | 5/2000 | Nosted ................. A61L 29/085 206/210 |
| 6,065,597 A | 5/2000 | Pettersson et al. |
| 6,090,075 A | 7/2000 | House |
| 6,391,010 B1 | 5/2002 | Wilcox |
| 6,578,709 B1 | 7/2003 | Kavanagh et al. |
| 6,602,244 B2 | 8/2003 | Kavanagh et al. |
| 6,634,498 B2 | 10/2003 | KayerØd et al. |
| 6,638,269 B2 | 10/2003 | Wilcox |
| 6,739,112 B1 * | 5/2004 | Marino .................. A01N 1/02 128/898 |
| 6,848,574 B1 | 2/2005 | Israelsson et al. |
| 6,849,070 B1 | 2/2005 | Hansen et al. |
| 6,887,230 B2 | 5/2005 | Kubalak et al. |
| 7,001,370 B2 | 2/2006 | Kubalak et al. |
| 7,094,220 B2 | 8/2006 | Tanghoj et al. |
| 7,150,739 B2 | 12/2006 | O'Neil |
| 7,160,590 B2 | 1/2007 | Vanhamel et al. |
| 7,311,698 B2 | 12/2007 | Tanghoj et al. |
| 7,328,794 B2 | 2/2008 | Lubs et al. |
| 7,334,679 B2 | 2/2008 | Givens, Jr. |
| 7,458,964 B2 | 12/2008 | Mosler et al. |
| 7,476,223 B2 | 1/2009 | McBride |
| 7,517,343 B2 | 4/2009 | Tanghoj et al. |
| 7,601,142 B2 | 10/2009 | House |
| 7,601,158 B2 | 10/2009 | House |
| 7,662,146 B2 | 2/2010 | House |
| 7,682,353 B2 | 3/2010 | Tanghoj et al. |
| 7,766,163 B2 | 8/2010 | Tanghoej |
| 7,770,726 B2 | 8/2010 | Murray et al. |
| 7,823,722 B2 | 11/2010 | Bezou et al. |
| 7,886,907 B2 | 2/2011 | Murray et al. |
| 7,918,831 B2 | 4/2011 | House |
| 7,922,712 B2 | 4/2011 | Tanghoj et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,066,693 B2 | 11/2011 | Tanghoj et al. |
| 8,127,922 B2 | 3/2012 | Nordholm et al. |
| 8,177,774 B2 | 5/2012 | House |
| 8,201,689 B2 | 6/2012 | Kaern |
| 8,205,745 B2 | 6/2012 | Murray et al. |
| 8,230,993 B2 | 7/2012 | Tanghoej |
| 8,317,775 B2 | 11/2012 | House |
| 8,356,457 B2 | 1/2013 | Murray et al. |
| 8,414,562 B2 | 4/2013 | House |
| 8,459,455 B2 | 6/2013 | FrÖjd |
| 8,523,843 B2 | 9/2013 | Kavanagh et al. |
| 8,567,602 B2 | 10/2013 | Niederberger et al. |
| 8,579,115 B2 | 11/2013 | Murphy et al. |
| 8,668,683 B2 | 3/2014 | Golden |
| 8,720,685 B2 | 5/2014 | Murray et al. |
| 8,740,863 B2 | 6/2014 | Nestenborg et al. |
| 9,033,149 B2 | 5/2015 | Terry |
| 9,314,585 B2 | 4/2016 | Nestenborg et al. |
| 9,854,483 B2 | 12/2017 | Chaudhuri et al. |
| 2005/0109648 A1 | 5/2005 | Kerzman et al. |
| 2005/0199521 A1 * | 9/2005 | Givens, Jr. ......... A61M 25/0017 206/364 |
| 2006/0058777 A1 | 3/2006 | Nielsen |
| 2006/0163097 A1 * | 7/2006 | Murray ............. A61M 25/0009 206/364 |
| 2007/0033906 A1 * | 2/2007 | Kernick ................ B65B 7/2878 53/485 |
| 2007/0074991 A1 * | 4/2007 | Heisserer .............. A61F 2/0095 206/438 |
| 2009/0000970 A1 | 1/2009 | Bordeau et al. |
| 2010/0293892 A1 | 11/2010 | Curry et al. |
| 2013/0144271 A1 | 6/2013 | Passadore et al. |
| 2013/0153446 A1 | 6/2013 | Utas et al. |
| 2013/0292286 A1 * | 11/2013 | Van Groningen ........................ A61M 25/0111 206/438 |
| 2014/0257250 A1 | 9/2014 | Palmer |
| 2014/0331602 A1 * | 11/2014 | Newman ................ B65B 51/22 53/405 |
| 2015/0351893 A1 * | 12/2015 | Smith .................. A61F 2/0095 623/16.11 |
| 2016/0220784 A1 | 8/2016 | Palmer |
| 2017/0296776 A1 | 10/2017 | Palmer |
| 2017/0341839 A1 * | 11/2017 | D'Souza ................ B65D 81/20 |

FOREIGN PATENT DOCUMENTS

| | | |
|---|---|---|
| EP | 1498151 A2 | 1/2005 |
| EP | 0909249 B1 | 4/2005 |
| EP | 2609956 A1 | 3/2013 |
| GB | 1465544 | 2/1977 |
| WO | 9806642 | 2/1998 |
| WO | 2006121508 A2 | 11/2006 |
| WO | 2013158270 A1 | 10/2013 |

* cited by examiner

PACKAGED PRECISION-LUBRICATED READY-TO-USE INTERMITTENT URINARY CATHETER

BACKGROUND

Intermittent catheters are typically used by patients suffering from urinary incontinence or by individuals unable to enjoy voluntary urination. In our highly mobile culture, the ability to have the freedom to leave home for the day or longer is an important part of life. To accommodate this need single use, pre-lubricated catheters have been developed to allow patients to perform self catheterization. An individual requiring catheterization will typically utilize several catheters each and every day. This results in the usage of a large number of catheters over time, driving a demand for inexpensive catheters without sacrificing safety and comfort.

The high daily utilization rate for intermittent urinary catheters also results in the need for individuals requiring catheterization to transport several catheters with them whenever they leave the house for any extended period of time. Packaged catheters tend to be large and bulky, rendering it difficult to discretely transport a supply of catheters.

Accordingly, a need exists for an inexpensive and efficiently packaged intermittent urinary catheter, particularly one that is self-contained and ready for use immediately upon removal from the packaging.

A particular complication encountered with the production and transport of inexpensive, single use, pre-lubricated, ready for use catheters for self-catheterization is constraining the lubricant to the insertion portion of the packaged catheter so as to prevent lubrication of the fixture end portion of the catheter which must be gripped during insertion and removal of the catheter.

Accordingly, a particular need exists for an inexpensive method for packaging a single use, pre-lubricated, ready for use catheter for self-catheterization that constrains the lubricant to contact with the insertion portion of the packaged catheter during packaging, and results in a packaged catheter that restrains migration of the lubricant within the package into contact with the fixture end of the catheter under normal storage and transport conditions.

SUMMARY OF THE INVENTION

A first aspect of the invention is an efficiently packaged, ready to use intermittent urinary catheter. The packaged catheter includes, and except for appropriate labeling and marking preferably only includes, (i) an intermittent urinary catheter, (ii) packaging formed from first and second layers of film, and (iii) a lubricant. The catheter has a longitudinal axial length, an insertion end, a funnel end and a top view profile, and is hermetically packaged between the first and second layers of film within a retention chamber formed from the films. The retention chamber has a top view profile conforming to the top view profile of the catheter and retains a supply of lubricant. In an alternative embodiment, the lubricant is predominately retained within an enlarged lubricant retaining compartment formed in the retention chamber intermediate the insertion and funnel ends of the catheter.

A second aspect of the invention is a method of efficiently packaging a precision lubricated ready to use intermittent urinary catheter having an insertion end, an insertion end length, a fixture end, and a fixture end length. The method includes the steps of (a) obtaining a base film having a pocket with a first end and a second end, wherein the pocket is configured to retain the intermittent urinary catheter with the insertion end proximate the first end and the fixture end proximate the second end, (b) injecting a limited amount of lubricant into the pocket proximate the first end of the pocket so as to form a lubricant containing pocket, (c) placing the intermittent urinary catheter into the lubricant containing pocket so as to form a catheter containing pocket, with the insertion end of the intermittent urinary catheter proximate the first end and the fixture end of the intermittent urinary catheter proximate the second end, (d) sealing a cover film to the base film with an unsealed opening proximate the second end of the pocket so as to form an enclosed catheter containing retention chamber accessible through the opening, (e) drawing a vacuum on the enclosed catheter containing retention chamber through the opening sufficient to compress the retention chamber and cause lubricant to circumferentially flow around and coat a portion of the exterior surface area of the insertion end length of the catheter within the retention chamber without reaching and coating the fixture end length of the catheter within the retention chamber, and thereafter (f) sealing the opening so as to form a hermetically packaged intermittent urinary catheter having a circumferentially lubricated insertion end length and a lubricant-free fixture end length.

DETAILED DESCRIPTION OF A PREFERRED EMBODIMENT

Nomenclature

10 Packaged Intermittent Urinary Catheter
20 Catheter
$20_{Pf}$ Top View Profile of Catheter
$20x$ Axial Length of Catheter
21 Insertion End of Catheter
$21x$ Axial Length of Insertion End Portion of Catheter
22 Fixture End or Funnel End of Catheter
$22x$ Axial Length of Fixture End Portion of Catheter
$25x$ Pre-vacuum Axial Length of Catheter In Contact with Lubricant Within the Pocket (Alpha Length)
30 Fixture or Funnel
40 Base Layer of Packaging 50 Pocket in Base Layer of Packaging
$50_{Pf}$ Top View Profile of Pocket
51 First End of Pocket
52 Second End of Pocket
60 Cover Layer of Packaging
70 Packaging
$70_{Py}$ Peripheral Edge of Packaging
75 Margins of Packaging
$75w$ Width of Margins
80 Retention Chamber
$80_{Pf}$ Top View Profile of Retention Chamber
$80_{Py}$ Periphery of Retention Chamber
$80_{Lube}$ Lubricant Containing Compartment
$80_{Neck}$ Metering Neck Area of Retention Chamber
81 First End of Retention Chamber
82 Second End of Retention Chamber
83 Sides of Retention Chamber
90 Lubricant
x Longitudinal or Axial Direction
y Lateral (Radial) Direction
z Transverse (Radial) Direction Definitions As utilized herein, including the claims, the term "fixture" means and refers to the well known commercially available components commonly attached to the proximal non-insertion end of urinary catheters, including specifically but not exclusively funnels, luer locks, clamps, valves, etc.

As utilized herein, including the claims, the term "predominant" means at least 80%.

Description

Packaged Catheter

Figure 1:
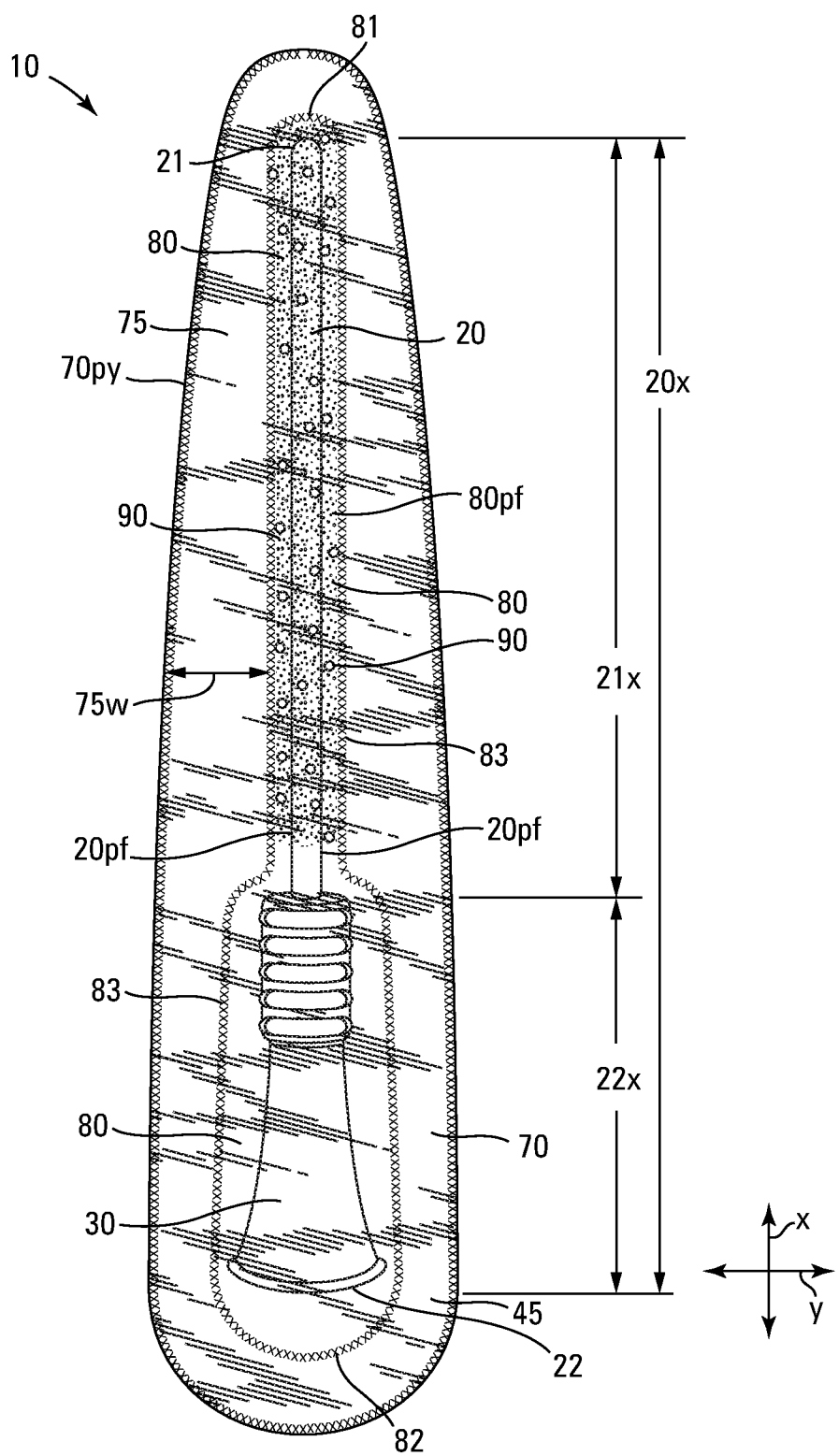
FIG. 1 is a top view of one embodiment of the invention.
Figure 2:
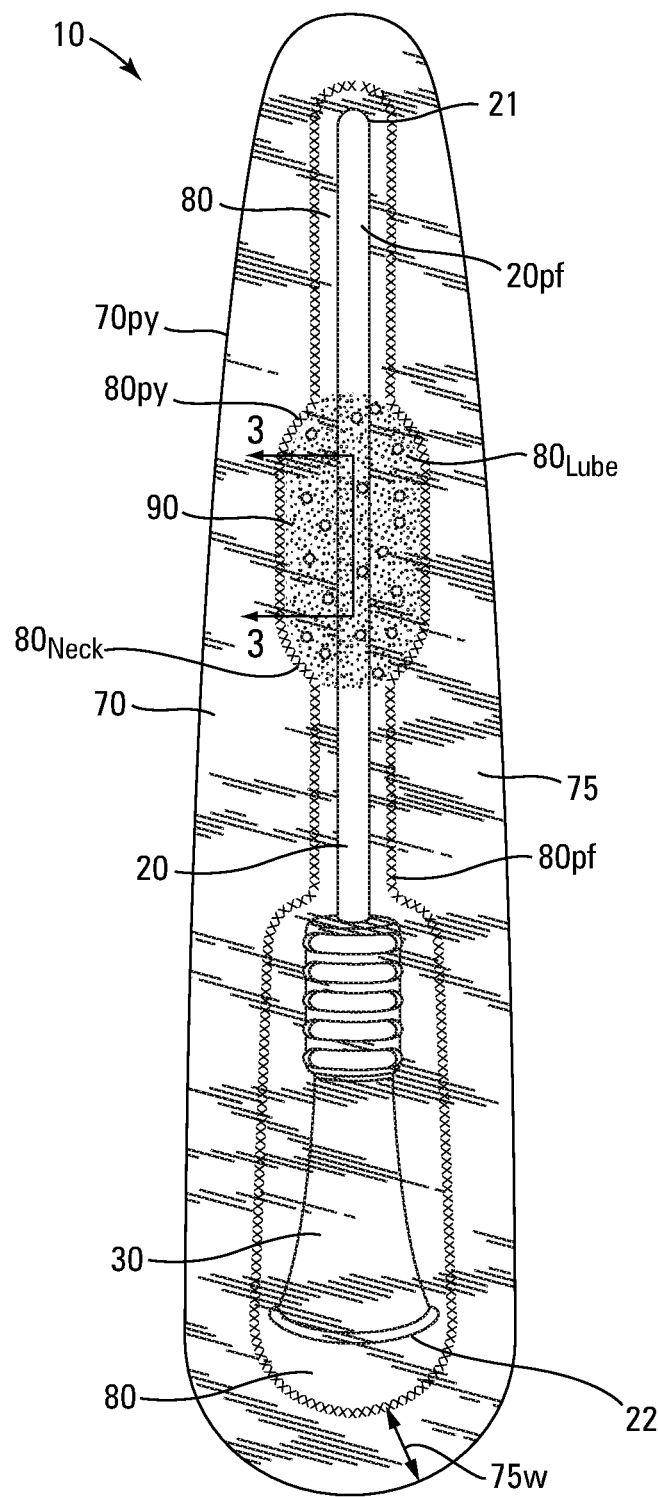
FIG. 2 is a top view of another embodiment of the invention
Figure 3:
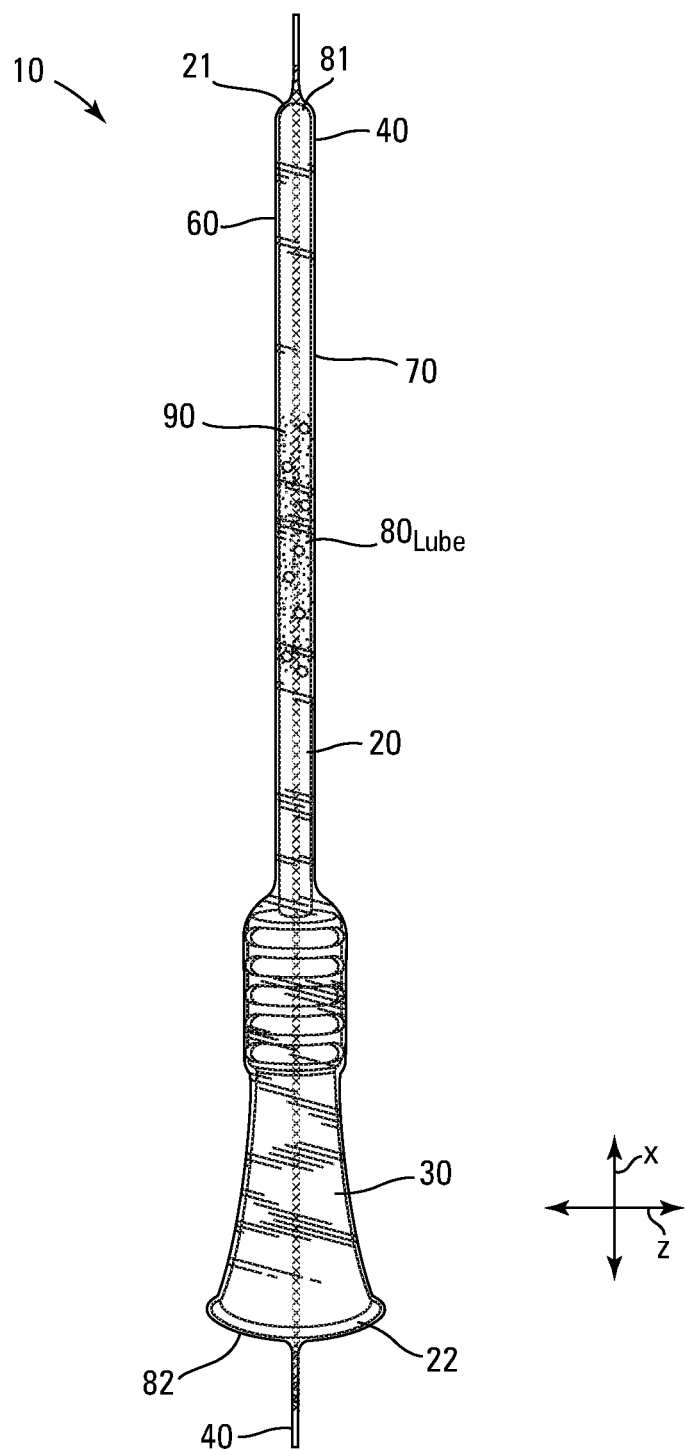
FIG. 3 is a side view of the invention depicted in FIG. 2.
Figure 4:
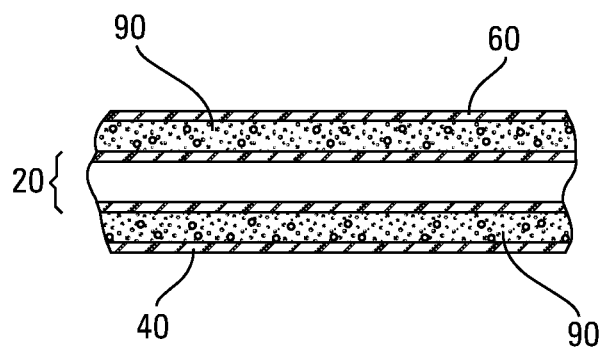
FIG. 4 is an enlarged cross-sectional side view of a portion of the invention depicted in FIGS. 2 and 3 taken along line 4-4.

The invention is an efficiently packaged, ready to use intermittent urinary catheter 10. Referring to FIGS. 1-3, the packaged catheter 10 includes, and in a preferred embodiment only includes the functional components of, (i) an intermittent urinary catheter 20 equipped with a fixture 30 at one end, (ii) packaging 70 formed from a base layer 40 and cover layer 60 of film, and (iii) a lubricant 90.

The catheter 20 has an axial length $20x$ with an insertion end 21, an insertion end axial length portion $21x$, a fixture end 22, and a fixture end axial length portion $22x$. The catheter 20 defines a top view profile $20_{Pf}$. The packaging 70 may be used with substantially any commercially available catheter 20, but is particularly suited for use with shorter female urinary catheters.

The catheter 20 is hermetically packaged within a retention chamber 80 formed between base layer 40 and cover layer 60 films sealed together, preferably by heat seal, within a peripheral margin 75 of the packaging 70. The films 40 and 60 may have originated from separate and independent rolls or sheets of film, or they may have been formed by simply folding a single length of film back upon itself. The packaging 70 formed by the base layer 40 and cover layer 60 films defines an outer peripheral edge $70_{Py}$. The retention chamber 80 has a periphery $80_{Py}$ defining a top view profile $80_{Pf}$ that generally conforms to the top view profile $20_{Pf}$ of the catheter 20, except for an optional enlarged compartment $80_{Lube}$ intermediate the insertion 21 and funnel 22 ends of the catheter 20 in which lubricant 90 can be stored for coating the catheter 20 when it is withdrawn from the packaging 70 for use. The optional enlarged compartment $80_{Lube}$ is preferably axially aligned with the balance of the retention chamber 80 such that the catheter 20 passes through the enlarged compartment $80_{Lube}$.

Referring to FIGS. 1 and 2, the margins 75 have a preferred width $75w$ of between 0.2 and 5 cm, most preferred between about 0.3 and 2 cm, around the entire periphery of the retention chamber 80.

The packaging layers 40 and 60 may be constructed from the same or different films, with the films selected from materials that are impervious to the lubricant 90, and suitable for hermetically sealing the catheter 20 within a retention chamber 80 formed from the films 40 and 60. Suitable materials include specifically but not exclusively, films of polyester, polyethylene, polypropylene, Surlyn®, Tyvek®, aluminum, Mylar®, etc.

Referring to FIGS. 1 and 2, the retention chamber 80 has a top view profile $80_{Pf}$ that tightly matches the top view profile $20_{Pf}$ of the catheter 20 along a predominant portion of the axial length $20x$ of the catheter 20 for purposes of maintaining lubricant 90 retained within the retention chamber 80 in close proximity to the catheter 20 so that the lubricant 90 will adhere to and coat the insertion end portion $21x$ of the catheter 20 as the catheter 20 is withdrawn from the packaging 70. The profiles are preferably matched such that the axial cross-sectional area of the retention chamber 80 (i.e., the cross-sectional area of the retention chamber 80 in a plane extending in the lateral y and transverse z directions and perpendicular to the longitudinal x axis of the catheter 20) is between 1.2 and 1.8 times the corresponding axial cross-sectional area of the catheter 20 along at least 50%, preferably along at least 80% and preferably along at least 90% of the axial length of the insertion end portion $21x$ of the catheter 20.

Referring to FIG. 2, when the retention chamber 80 includes an expanded lubricant containing compartment $80_{Lube}$, the axial cross-sectional area of the lubricant containing compartment $80_{Lube}$ is between 2 and 4 times the largest axial cross-sectional area of the catheter 20 lying within the compartment $80_{Lube}$ as packaged. The lubricant containing compartment $80_{Lube}$ necks down at the longitudinal x end of the compartment $80_{Lube}$ proximate the fixture end 22 of the catheter 20, preferably necking down at both longitudinal x ends, to an axial cross-sectional area that is between 1.2 and 1.8 times the largest axial cross-sectional area of the catheter 20 lying within the compartment $80_{Lube}$ as packaged. This necked down area $80_{Neck}$ formed from the packaging films 40 and 60, serves to meter the coating of lubricant 90 on the catheter 20 as the catheter 20 is withdrawn from the packaging 70 for use.

Method of Packaging Ready to Use Catheter

A preferred method of packaging the ready to use intermittent urinary catheter 10 employs a novel lubricant placement and spreading technique.

Figure 5:
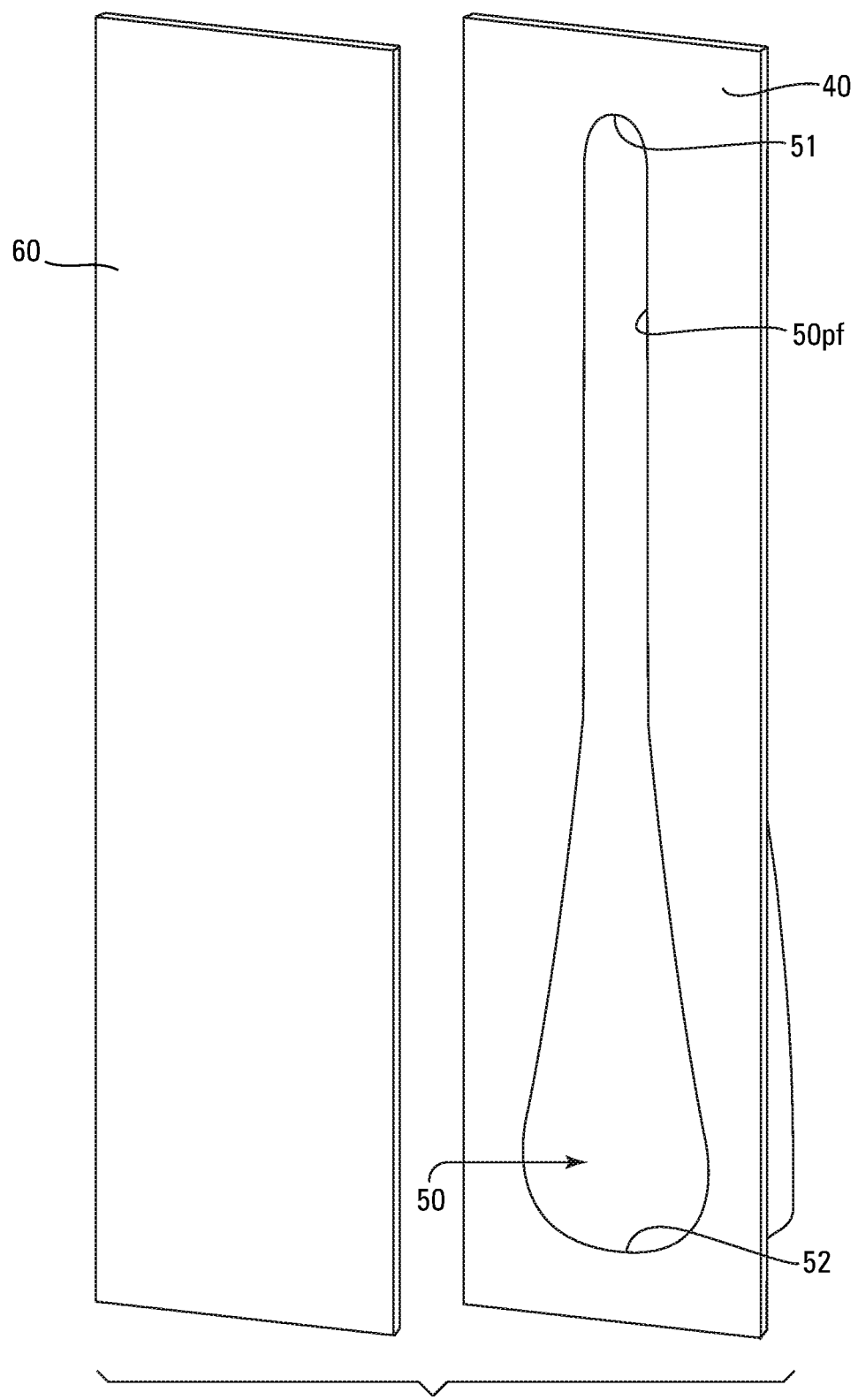
FIG. 5 is a perspective view of one embodiment of a base layer and a cover layer suitable for use in hermetically packaging an intermittent urinary catheter in accordance with the invention.

Referring to FIG. 5, the method employs a base film 40, a cover film 60 and lubricant 90.

The base film 40 has a blister or pocket 50 with a first end 51 and a second end 52. The pocket 50 preferably has a top view profile $50_{Pf}$ conforming to the top view profile $20_{Pf}$ of the intermittent urinary catheter 20, and is configured to retain at least a portion and preferably the entire urinary catheter 20 within the pocket 50, with the insertion end 21 of the catheter 20 proximate the first end 51 of the pocket 50 and the fixture end 22 of the catheter 20 proximate the second end 52 of the pocket.

The cover film 60 is preferably a planar sheet.

Figure 6:
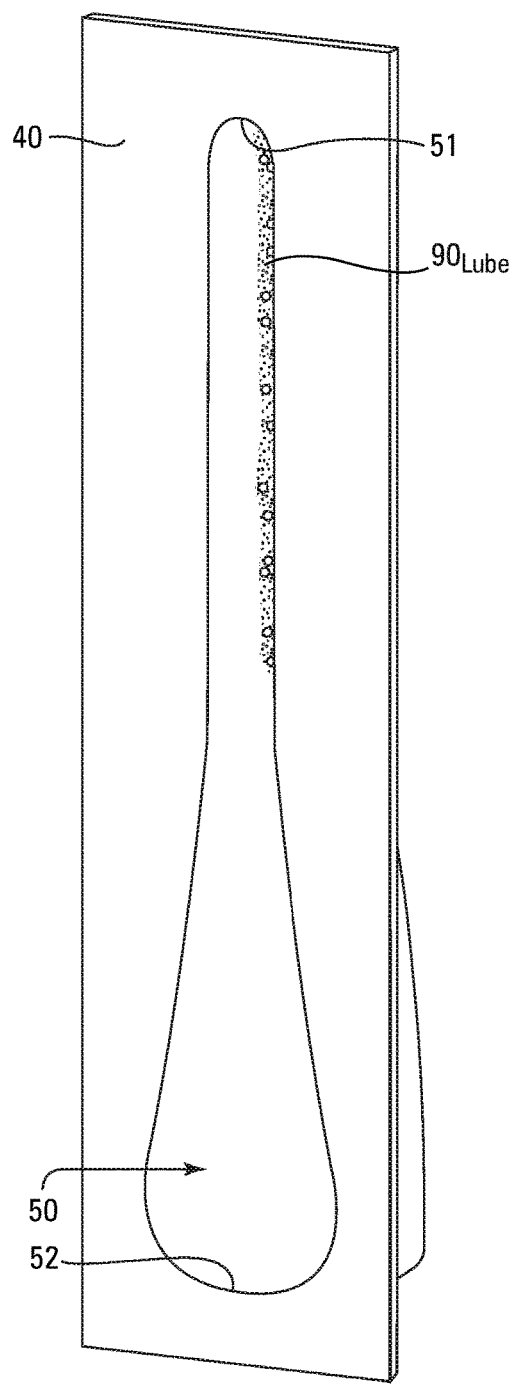
FIG. 6 is a perspective view of the base layer depicted in FIG. 5 after injection of lubricant into the pocket of the base layer in accordance with the invention.

Referring to FIG. 6, an amount of lubricant 90 is inserted into the pocket 50 in the base film 40 along a substantial axial length x of the insertion end portion $21x$ of the pocket 50 so as to form a lubricant containing pocket 50. The lubricant 90 is preferably applied so as to extend along at least about 30% of the axial length of the insertion end portion 21x of catheter 20, with a preference for a continuously applied axial x length of at least 50% of the axial length of the insertion end portion 21x, more preferably at least 70% and most preferably at least 80%.

Figure 7:
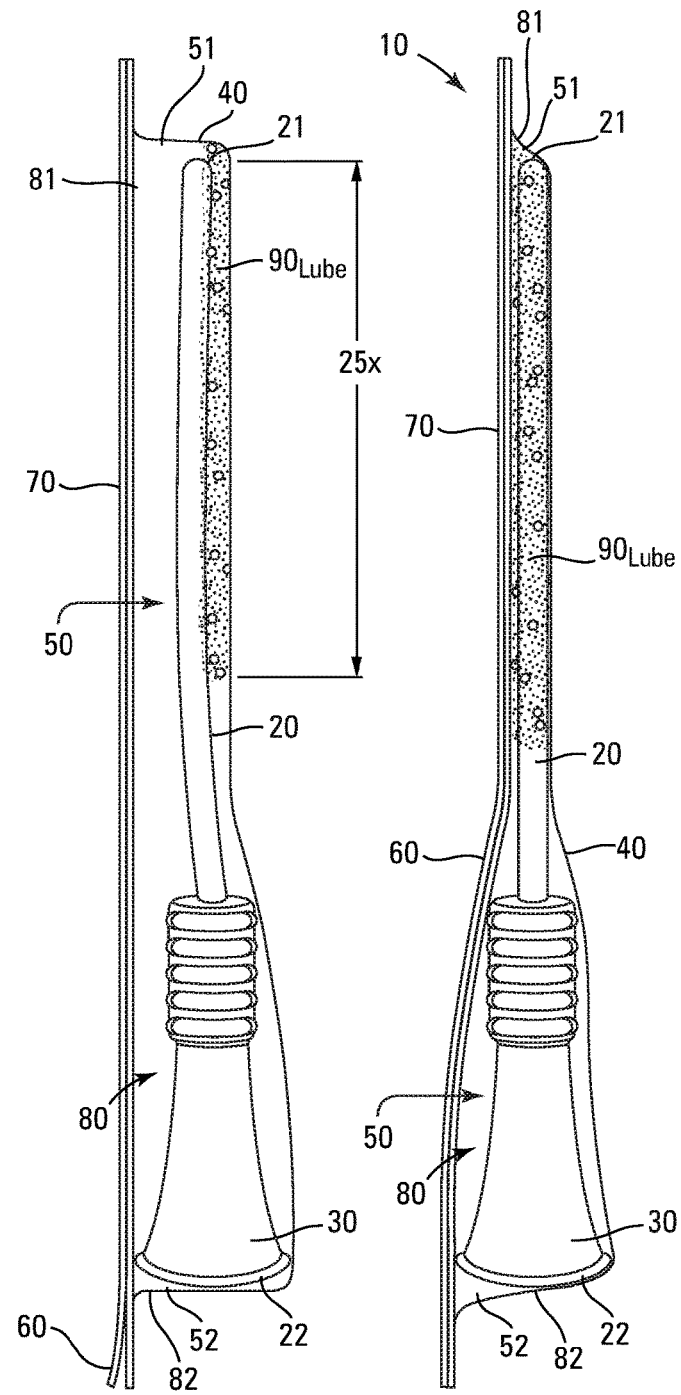
FIG. 7 is a side view of the base layer depicted in FIG. 6 after placement of a catheter into the lubricant containing pocket of the base layer and heat sealing of the cover layer to the base layer, but prior to pulling of a vacuum in accordance with the invention.

Referring to FIG. 7, a urinary catheter 20 is then placed into the lubricant containing pocket 50 with an alpha axial length 25x of the insertion end portion 21x resting atop and in fluid communication with the lubricant 90 so as to form a catheter containing pocket 50, with the insertion end 21 of the urinary catheter 20 proximate the first end 51 of the pocket 50 and the fixture end 22 of the urinary catheter 20 proximate the second end 52 of the pocket 50. The alpha axial length 25x of the insertion end portion 21x resting atop and in fluid communication with the lubricant 90 is preferably between 30% and 90% of the insertion end length of the catheter, more preferably between 50% and 80% and most preferably 40% and 60%.

The cover film 60 is placed over the base film 40 and sealed, such as by heat sealing, to the base film 40 around the profile of the pocket $50_{Pf}$ except along a length proximate the second end 52 of the pocket 50 so as to form a catheter containing retention chamber 80 between the base film 40 and the cover film 60 which is sealed except for an opening proximate the second end 82.

Figure 8:
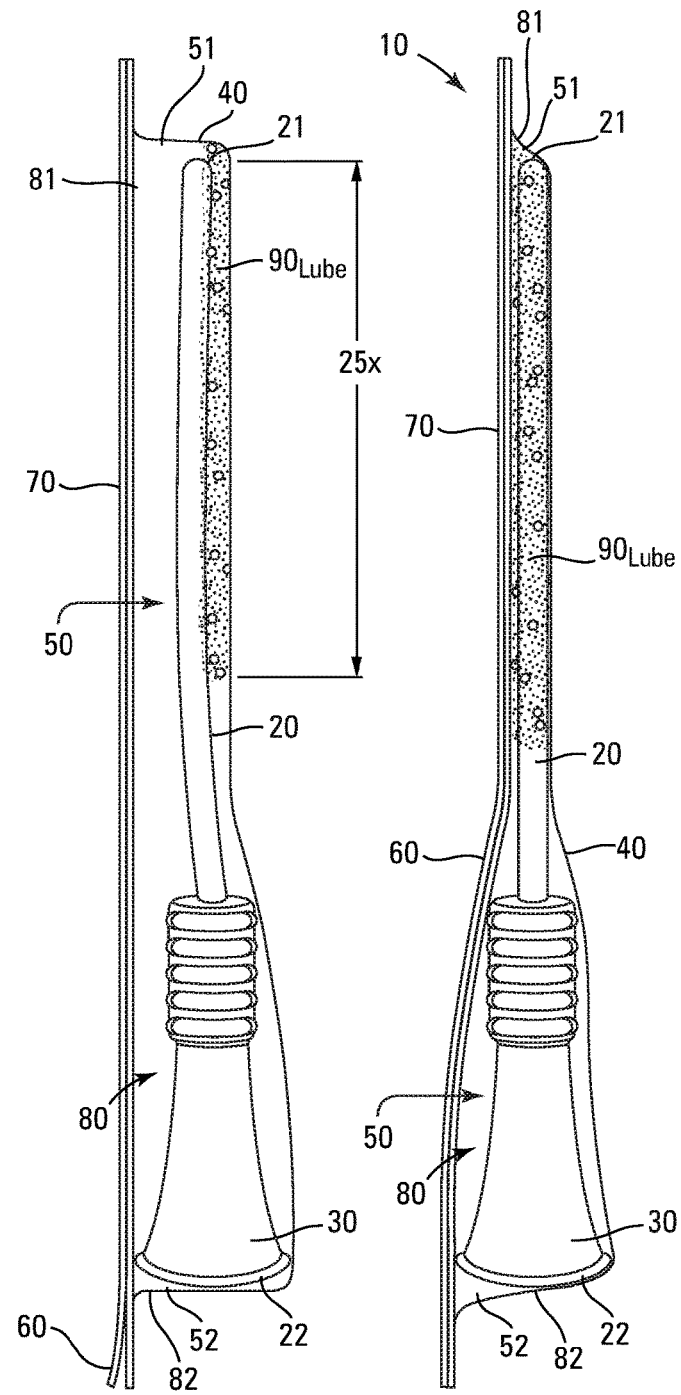
FIG. 8 is a side view of the invention depicted in FIG. 7 after pulling of a vacuum and complete sealing of the catheter within the packaging in accordance with the invention.

Referring to FIG. 8, a vacuum is drawn on the catheter containing retention chamber 80 through the opening sufficient to compress the retention chamber 80 and thereby cause lubricant 90 to circumferentially flow around and coat a substantial percentage of the surface area of the alpha axial length 25x of the insertion end portion 21x resting atop and in fluid communication with the lubricant 90, with a preference for coating at least 70% of the surface area of the alpha axial length 25x and most preferably 90%.

Pulling of a vacuum with resultant compression of the retention chamber 80 will also tend to draw lubricant 90 an axial distance x towards the second end 52 of the pocket 50. The vacuum should be applied at a pressure and for a duration sufficient to effect substantially complete circumferential coating of that portion of the insertion end portion 21x of the catheter 20 placed atop the lubricant 90, but without causing the lubricant 90 to travel an axial distance x that results in coating any portion of the fixture end 22 of the catheter 20.

The lubricant 90 preferably has a viscosity of between about 15,000 and about 500,000 centipoise at 72° F. When the viscosity is less than about 15,000 cp it is difficult to control the axial x length of the insertion end portion 21x of catheter 20 which is coated with lubricant 90 when pulling the vacuum, along with an increased likelihood that lubricant 90 will migrate into contact with the fixture end portion 22x of the catheter 20 under normal storage and transport conditions. Generally, when a high lubricity embodiment is desired the lubricant 90 preferably has a viscosity of between 15,000 and 50,000 centipoise at 72° F., and when superior control over lubricant 90 coverage during packaging and lubricant 90 migration during normal storage and handling is desired the lubricant 90 preferably has a viscosity of between 100,000 and 400,000 centipoise at 72° F.

The opening into the retention chamber 80 is then sealed, such as by heat sealing, to form a hermetically packaged intermittent urinary catheter 10 having a lubricated insertion end portion 21x and a lubricant-free fixture end portion 22x. The vacuum may be and preferably is at least partially released and more preferably is fully released prior to sealing of the opening.

I claim:

1. A method of hermetically packaging an intermittent urinary catheter having an insertion end, an insertion end length defining an exterior surface area, a fixture end, and a fixture end length, comprising the steps of:
   (a) obtaining a base film having a pocket with a first end and a second end, wherein the pocket is configured to retain the intermittent urinary catheter with the insertion end proximate the first end and the fixture end proximate the second end,
   (b) injecting a limited amount of lubricant into the pocket proximate the first end of the pocket so as to form a lubricant containing pocket,
   (c) placing the intermittent urinary catheter into the lubricant containing pocket so as to form a catheter containing pocket, with the insertion end of the intermittent urinary catheter proximate the first end and the fixture end of the intermittent urinary catheter proximate the second end,
   (d) sealing a cover film to the base film with an unsealed opening proximate the second end of the pocket so as to form an enclosed catheter containing retention chamber accessible through the opening,
   (e) drawing a vacuum on the enclosed catheter containing retention chamber through the opening sufficient to compress the retention chamber and cause lubricant to circumferentially flow around and coat a portion of the exterior surface area of the insertion end length of the catheter within the retention chamber without reaching and coating the fixture end length of the catheter within the retention chamber, and thereafter
   (f) sealing the opening so as to form a hermetically packaged intermittent urinary catheter having a circumferentially lubricated insertion end length and a lubricant-free fixture end length.

2. The method of claim 1 wherein the intermittent urinary catheter has a profile and the pocket has a profile conforming to the profile of the intermittent urinary catheter.

3. The method of claim 1 wherein an alpha length of the intermittent urinary catheter is placed atop and into fluid contact with the lubricant within the pocket in step (c) and the vacuum is sufficient to effect a circumferential flow of lubricant around the alpha length so as to coat at least 70% of the external surface area of the alpha length of the catheter.

4. The method of claim 3 wherein the vacuum is sufficient to effect a circumferential flow of lubricant around the alpha length so as to coat at least 90% of the external surface area of the alpha length of the catheter.

5. The method of claim 3 wherein the alpha length is between 30% and 90% of the insertion end length of the catheter.

6. The method of claim 3 wherein the alpha length is between 50% and 80% of the insertion end length of the catheter.

7. The method of claim 3 wherein the alpha length is between 40% and 60% of the insertion end length of the catheter.

8. The method of claim 1 wherein the lubricant has a viscosity of between 15,000 and 500,000 centipoise at 72° F.

9. The method of claim 1 wherein the lubricant has a viscosity of between 15,000 and 50,000 centipoise at 72° F.

10. The method of claim 1 wherein the lubricant has a viscosity of between 100,000 and 400,000 centipoise at 72° F.

11. The method of claim 1 wherein the cover film is heat sealed to the base film in step (d).

12. The method of claim 1 wherein the opening is heat sealed.

13. The method of claim 1 wherein the cover film is a planar sheet.

* * * * *